(12) United States Patent
Profitt et al.

(10) Patent No.: US 6,815,210 B1
(45) Date of Patent: Nov. 9, 2004

(54) TOTAL PROTEIN DETECTION METHODS AND DEVICES

(75) Inventors: James A. Profitt, Goshen, IN (US); Alexander H. Orn, Nappanee, IN (US); Jennifer Farr, Albion, IN (US)

(73) Assignee: Bayer Healthcare LLC, East Walpole, MA (US)

( * ) Notice: Subject to any disclaimer, the term of this patent is extended or adjusted under 35 U.S.C. 154(b) by 0 days.

(21) Appl. No.: 10/480,314

(22) PCT Filed: Jun. 21, 2002

(86) PCT No.: PCT/IB02/02321

§ 371 (c)(1),
(2), (4) Date: Dec. 11, 2003

(87) PCT Pub. No.: WO03/001213

PCT Pub. Date: Jan. 3, 2003

Related U.S. Application Data

(60) Provisional application No. 60/300,104, filed on Jun. 25, 2001.

(51) Int. Cl.$^7$ ........................ G01N 21/78; G01N 33/68
(52) U.S. Cl. .......................... 436/86; 436/169; 422/55; 422/56
(58) Field of Search ........................... 436/86, 15, 164, 436/169; 422/55, 56

(56) References Cited

U.S. PATENT DOCUMENTS

| | | |
|---|---|---|
| 3,438,737 A | 4/1969 | Atkinson |
| 3,485,587 A | 12/1969 | Keston |
| 5,077,222 A | 12/1991 | Lau |
| 5,087,575 A | 2/1992 | Lau |
| 5,279,790 A | 1/1994 | Corey et al. |
| 5,326,707 A * | 7/1994 | Franke et al. ................. 436/86 |
| 5,399,498 A | 3/1995 | Pugia |
| 5,424,125 A | 6/1995 | Ballard et al. |
| 5,424,215 A | 6/1995 | Albarella et al. |
| 5,593,895 A | 1/1997 | Cahill et al. |
| 5,716,851 A | 2/1998 | Pugia et al. |
| 5,750,405 A | 5/1998 | Albarella et al. |
| 5,908,787 A | 6/1999 | Cast et al. |

FOREIGN PATENT DOCUMENTS

| | | |
|---|---|---|
| EP | 0361244 A2 | 4/1990 |
| EP | 0785429 A1 | 7/1997 |
| EP | 0907081 A1 | 4/1999 |
| EP | 0877251 B1 | 11/2002 |
| JP | 04361160 A | 12/1992 |

OTHER PUBLICATIONS

"Clinical Nephrology Meetings 2001"; National Kidney Foundation; pp. 1, 2, 21, 207 & A20, Orlando, Florida, Apr. 2001.

Profitt, J. et al., "The Relative Utility or Urinary Total Protein and Albumin Dipstick Measurement In the Identification of Patients with Myleoma and Tubular Proteinuria", *Am. J. Kidney Dis.*, 37(4) A27 (2001).

Pugia, M.J. et al., "Screening for Proteinuria in Japanese School Children: A New Approach", *Clin. Chem. Lab. Med.*, 38/10 pp. 975–982 (2000).

Pugia, M.J. "Technology Behind Diagnostic Reagent Strips", *Lab Medicine*, 31/2, pp. 92–96 (2000).

Pugia, M.J. et al., "High Sensitivity Dye Binding Assay for Albumin in Urine", *J. Clin. Lab. Analysis*, 13/4, pp. 180–187 (1999).

Pugia, M.J. et al., "Screening School Children for Albuminuria; Proteinuria and Occult Blood with Dipsticks", *Clin Chem Lab Med*, 37/2, pp. 149–157 (1999).

Pugia, M.J. et al., "Encyclopedia of Urinalysis, Chapter 5b. New Developments in Urinalysis Strip Tests for Proteins" (date unknown).

Pugia, M.J. et al., "Comparison of Instrument–Read Dipsticks for Albumin and Creatinine in Urine With Visual Results and Quantitative Methods", *J. Clin Lab Analysis*, 12/5, pp. 280–284 (1998).

Sasaki, M. et al., "Measurement of the Albumin Content of Urinary Protein Using Dipsticks", *J. Clin. Lab. Analysis*, 13/5, pp. 246–250 (1999).

Watanabe, N. et al., "Urinary Protein as Measured with a Pyrogallol Red–Molybdate Complex, Manually and in a Hitachi 726 Automated Analyzer", *Clin. Chem.* 32/8 pp. 1551–1554 (1986).

\* cited by examiner

Primary Examiner—Maureen M. Wallenhorst

(57) ABSTRACT

An assay for the determination of protein in an aqueous test fluid which combines the test fluid with a buffer and a dye. The buffer is selected from citrulline, malonic acid, cyanoacetic acid, citraconic acid, methyl phosphonic acid, sarcosine, saccharin, or combinations thereof. The buffer is added in sufficient quantity to maintain the pH of the assay including the test fluid at a selected target pH range within a range of from about 2.0 to about 3.0. The dye has a pKa which enables it to operate as a protein indicator at the target pH range. The dye also has affinity for protein such that it will provide a detectable response in the presence of greater than about 15 mg/dL protein to thereby render the assay suitable for the detection of total protein in the test fluid. The buffer and dye may be absorbed in a test strip of absorbent material.

35 Claims, No Drawings

TOTAL PROTEIN DETECTION METHODS AND DEVICES

This application claims the benefit of Provisional application Ser. No. 60/300,104 filed Jun. 25, 2001.

FIELD OF THE INVENTION

The present invention relates generally to methods and devices of detecting proteins. Specifically, the invention is directed to methods and devices for detecting proteins at lower pH's using various buffers.

BACKGROUND OF THE INVENTION

Methods for the detection of urinary proteins are often more sensitive to albumin than to other urinary proteins. It is important, however, to detect proteins other than albumin, especially in the case of Bence-Jones proteinuria. The detection of proteins should cover a wide range of protein concentrations since the decision levels and recommended actions to be taken by clinicians will vary depending on the concentration of protein detected in a patient's urine. For example, persistent proteinuria greater than 50 mg/dL represents strong evidence of renal disease whereas a protein level of greater than 300 mg/dL is consistent with a diagnosis of nephrotic syndrome. A concentration of protein in urine of greater than 800 mg/dL suggests massive protein loss and warrants a renal biopsy and/or steroid therapy. Accordingly, it is apparent that a test for protein in urine should be effective over a wide range of protein values.

Various methods for the determination of protein in aqueous fluid have been reported in the literature. These methods include the Kjeldahl method, biuret method, Lowery method, dyestuff combination method, UV method and fluorometric method. In general, proteins react with various substance including dyes such as bromphenol blue, coomassie brilliant blue and eosine, as well as metal ions such as silver (I), copper (II), zinc (II) and lead (II).

Urine contains amounts of salt that vary between individuals. Some of these salts may act as a buffer when a diagnostic assay demands operation at a pH different than that of the urine sample. For example, urine sample with salts such as bicarbonate, acetate or phosphate tend to resist the lowering of pH. Creatinine, a common component of urine, may also act as a buffer in resisting the lowering of pH. The result of this buffering is that some urine samples will cause a strip pH to be higher than optimal. A higher than optimal strip pH may result in color generation of the protein indicator dyes, providing a false indication of the presence of protein. It is desired to have a buffing system that reduces such urine effects, while not interacting with the chemistry occurring.

Accordingly, a need exists for a method and device for detecting proteins over a wide range of clinical concentrations and pH's.

SUMMARY OF THE INVENTION

According to one embodiment, an assay for the determination of protein in an aqueous test fluid comprises combining the test fluid with a buffer and a dye. The buffer is selected from citrulline, malonic acid, cyanoacetic acid, citraconic acid, methyl phosphonic acid, sarcosine, saccharin, or combinations thereof. The buffer is added in sufficient quantity to maintain the pH of the assay including the test fluid at a selected target pH range within a range of from about 2.0 to about 3.0. The dye has a pKa which is enables it to operate as a protein indicator at the target pH range. The dye has an affinity for protein such that it will provide a detectable response in the presence of greater than about 15 mg/dL protein, to thereby render the assay suitable for the detection of total protein in the test fluid.

According to another embodiment, a dry device for use in determining protein levels in a fluid test sample comprises an absorbent material having absorbed therein a buffer and a dye. The buffer is selected from citrulline, malonic acid, cyanoacetic acid, citraconic acid, methyl phosphonic acid, sarcosine, saccharin, or combinations thereof. The buffer is added in sufficient quantity to maintain the pH of the assay including the test fluid at a selected target pH range within a range of from about 2.0 to about 3.0. The dye has a pKa which enables it to operate as a protein indicator at the target pH range. The dye has an affinity for protein such that it will provide a detectable response in the presence of greater than 15 mg/dL protein upon contact between the device and the fluid test sample, to thereby render the device suitable for the detection of total protein in the fluid test sample.

According to a further embodiment, an assay for the determination of protein in an aqueous test fluid comprises combining the test fluid with a buffer and a dye. The buffer is selected from citrulline, malonic acid, or combinations thereof. The buffer is added in sufficient quantity to maintain the pH of the assay including the test fluid at a selected target pH range within a range of from about 2.0 to about 3.0. The dye has a pKa which enables it to operate as a protein indicator at the target pH range and which has an affinity for protein such that it will provide a detectable response in the presence of greater than about 15 mg/dL protein, to thereby render the assay suitable for the detection of total protein in the test fluid.

According to yet a further embodiment, a dry device for use in determining protein levels in a fluid test sample comprises an absorbent material having absorbed therein a buffer and a dye. The buffer is selected from citrulline, malonic acid or combinations thereof. The buffer is added in sufficient quantity to maintain the pH of the assay including the test fluid within a selected target pH range within a range of from about 2.0 to about 3.0. The dye has a pKa which enables it to operate as a protein indicator at the target pH range and which has affinity for protein such that it will provide a detectable response in the presence of greater than 15 mg/dL protein upon contact between the device and the fluid test sample, to thereby render the device suitable for the detection of total protein in the fluid test sample.

DETAILED DESCRIPTION OF THE ILLUSTRATED EMBODIMENT

The assay for protein of the present invention can be carried out in either the wet or dry format. It is most conveniently carried out in the form of an absorbent test strip impregnated with (a) a buffer selected from citrulline, malonic acid, cyanoacetic acid, citraconic acid, methyl phosphonic acid, sarcosine, saccharin, or combinations thereof, and (b) a dye having a pKa which enables it to operate as a protein indicator (e.g., a color indicator) at a pH of from about 2.0 to about 3.0.

Buffers

The buffer to be used in the present invention is added in sufficient quantity to maintain the pH of the assay including the test fluid within a range of from about 2.0 to about 3.0. The buffer may have a prior adjustment of pH that is commonly accomplished by adding acid or base to a solution of the buffer chemical to achieve a particular pH, or by adding a mixture of the buffer chemical and its salt in selected proportions to give a particular pH. The buffer is preferably added to maintain the pH of the assay including the test fluid within about +/−0.2 pH units of the selected target pH. The buffer is preferably added in sufficient quantity to maintain the pH of the assay including the test fluid within a range of from about 2.4 to about 3.0.

The preferred buffers are citrulline, malonic acid or combinations thereof. Buffers may be selected from citrulline, malonic acid, cyanoacetic acid, citraconic acid, methyl phosphonic acid, sarcosine, saccharin, or combinations thereof. Various concentrations of these buffers may be used, but the concentrations of the buffers are generally from about 200 to about 500 mM.

Citrulline may be in the form of L-citrulline, D-citrulline and D,L-citrulline and is represented by structure A.

Structure A

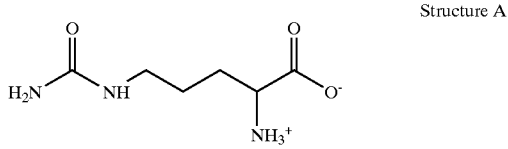

Malonic acid that is useful in the present invention is represented by Structure B,

Cyanoacetic acid that is useful in the present invention is represented by Structure C,

Citraconic acid that is useful in the present invention is represented by Structure D.

Structure D

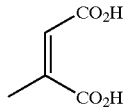

Methyl phosphonic acid that is useful in the present invention is represented by Structure E. environment than when free in solution, and effectively develop a lower pKa for the ionization essential to color change. If the dye, in the absence of a protein, also responds as a pH sensitive color indicator within the selected target pH range, then added proteins will generally not be detected accurately.

The dyes to be used in the present invention generally provide a detectable response in the presence of total protein from about 2 to about 500 mg/dL protein. The dyes preferably provide a detectable and particularly useful response to total protein from about 15 to about 300 mg/dL protein. It is contemplated that the amount of dye may be varied to give a detectable and useful response outside of such a preferred range.

Examples of these dyes include substituted phenolsulfonephthaleins, pyrogallol red or combinations thereof. It is contemplated that other dyes that tend to have a detectable indication in the dye absorbance or fluorescence spectrum (as indicating transition) in the pH range of from about 2 to about 3 in the absence of protein and a different indication, under otherwise the same conditions, but in the presence of protein may be used in the present invention. The pH for giving a different detectable response between the presence and absence of protein, should be within the pH range maintainable by the buffer being used in the present invention.

For example, it is contemplated that dyes such as bromochlorophenol blue (3',3"-dibromo-5',5"-dichlorophenolsulfonephthalein); bromophenol blue (tetrabromophenol blue); basic fuchsin (basic red 9); basic violet 14; martius yellow (acid yellow 24); phloxine B (acid red 92); methyl yellow (solvent yellow 2); congo red (direct red 28); methyl orange (acid orange 52); and ethyl orange (4-(4-diethylaminophenylazo)benzenesulfonic acid) may be useful in the present invention. Such dyes may be used in combination with dyes such as phenolsulfonephthaleins and pyrogallol red.

The phenolsulfonephthalein indicators particularly useful in the present invention are represented by the following structures, H and I:

Structure H

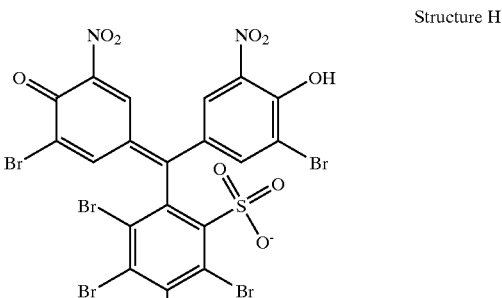

Structure I

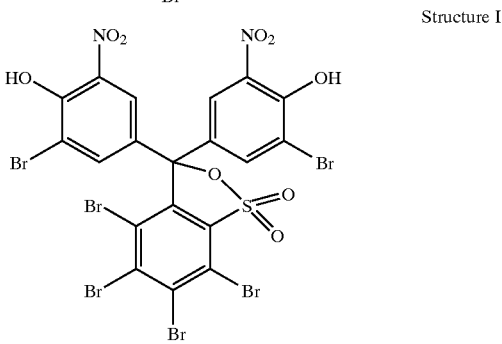

Structure H represents the structure of a phenolsulfonephthalein derivative in protic solvents such as water or an alcohol, while Structure I represents the form that predominates in the dry state or in aprotic solvents such as ethers and acetonitrile. The phenolsulfonephthalein "protein error" indicators are pH indicators that include an ionizable proton having a pKa value such that at particular pH's the proton is not ionized unless in the presence of protein.

The pKa value of a general phenolsulfonephthalein indicator shown below, Structure J, is the pH at which one half of the number of indicator molecules include the deprontated C ring phenolic hydroxyl group. In the case of the phenolsulfonephthalein protein error indicators illustrated above, two deprotonation events occur to cause an observable color change. The first deprotonation removes the proton from the aryl sulfonic acid on the A ring to yield the ion illustrated below as Structure J.

Structure J

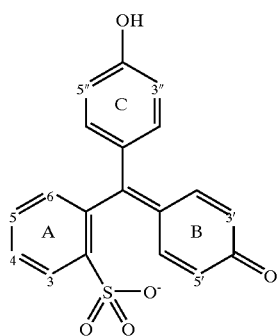

The pKa of this proton is less than one, resulting in the ionization of this moiety at all useful pH values. This ionizable group is also responsible for the aqueous solubility of these compounds. The second deprotonation involves the release of a proton from the C ring phenolic hydroxyl to yield the dianion as shown in Structures K and L below.

Structure K

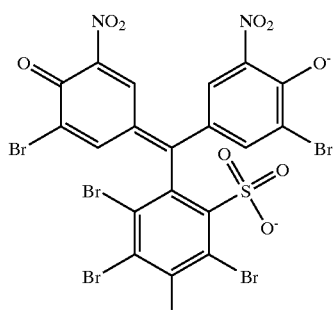

Structure L

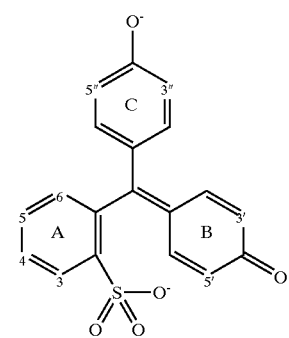

With this type of protein error indicator, the second deprotonization causes the observable color change that is indicative of the presence of protein in the sample being tested. The phenolsulfonephthalein protein error indicator is typically applied to an absorbent matrix material along with a buffer to provide an environment of constant pH, so that one can rely on the color change being the result of the presence of protein rather than the result of a pH change upon contact with the test fluid.

Only those phenolsulfonephthalein protein error indicators which have a second pKa allowing the second deprotonation, in the presence of protein, to take place at a pH within a range of from about 2.0 to about 3.0 are useful in the present invention. Those phenolsulfonephthalein protein error indicators that have a second pKa allowing the second deprotonation, in the absence of protein, to occur outside of the maintained pH may be useful in the invention. Preferably, the second pKa, in the absence of protein, takes place at a pH not within the range of from about 2.4 to about 3.0 and, most preferably, at a pH above 3.0. It is contemplated that an ionization sensitive to protein presence that also gives a detectable indication (e.g., a color response) may be a first, second, etc. deprotonation with a different assortment of ionizable substituents.

Many phenolsulfonephthalein protein error indicators have their second pKa in the appropriate range and are, therefore, suitable for use in the present invention. Useful phenolsulfonephthaleins include those that are substituted with electron withdrawing and/or electron donating groups such as amino, amido, aromatic, alkyl, hydroxyl, thio, carboxylic, alkoxy, ketoxy, acetyl, halogen, nitro, and cyano on the A, B or C rings of Structures J and L. It is contemplated that one or more of the rings may still contain a hydrogen. The particular substituent(s) and their positions on the dye molecule are not critical so long as the resulting dye exhibits a pKa in the appropriate range, and retains desirable physical properties, such as solubility, protein affinity and color. Unsubstituted phenolsulfonephthaleins are not suitable because their pKa's are not in the appropriate range. It has been discovered that the octa substituted sulfonephthalein indicators, ie., those phenolsulfonephthalein derivatives that are substituted at the 3', 3", 5', 5", 3, 4, 5 and 6 positions, are particularly suitable for use in the present invention. These indicators are preferably substituted with halogen and nitro groups and may be represented by Structure M:

Structure M

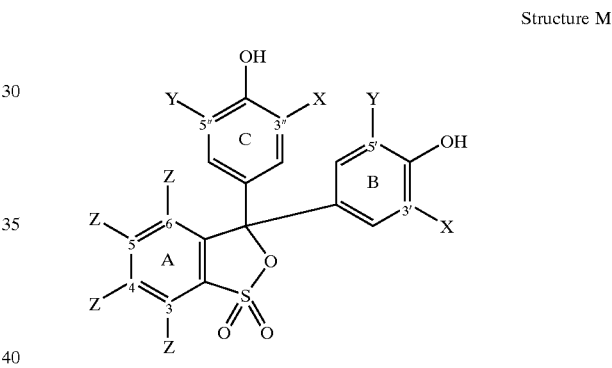

where: X is nitro and Y and Z are chlorine, bromine or iodine. Also useful are the nitro substituted polyhalogenated phenolsulfonephthaleins disclosed in U.S. Pat. No. 5,279,790 wherein Y is nitro and X and Z are chlorine, bromine or iodine. These indicators are said to have the ability to detect from about 2 to 500 mg/dL of protein in a fluid test sample. However, use of the assay system of the present invention would be desirable in situations in which proteinuria greater than 30 mg/dL is measured and microalbuminuria at 2 mg/dL is not measured.

For example, in the case of diagnosing children for renal disease, it is not desirable to measure microalbumin as this response may give a false indication of disease due to its variable nature. It is evident that the aromatic rings of the phenolsulfonephthalein indicators useful in the present invention can bear a variety of substituent groups. Such substituent groups are limited only by the ability of one of ordinary skill in the art to prepare stable compounds that have the appropriate protein error indicator properties to render them suitable for use in the present invention.

Some specific examples of the phenolsulfonephthalein dyes are those substituted at the 5', 5" positions with nitro and at the 3', 3", 3, 4, 5 and 6 positions with chloride, bromide or iodide. For example, phenolsulfonephthalein dyes that may be used include 5, 5"-Dinitro-3', 3", 3, 4, 5, 6-hexabromophenolsulfonephthalein or 5'-Nitro-5"-Iodo-3', 3", 3, 4, 5, 6,-hexabromophenolsulfonephthalein.

As discussed above, a dye that may be used is pyrogallol red. Pyrogallol red typically includes the use of a molybdate or tungstate salt that assists in providing rich color. U.S. Pat. No. 5,399,498 discloses that tungstate reacts with the indicator to form a complex whose color shifts in the presence of protein in a manner similar to that of molybdenum. U.S. Pat. No. 5,399,498 also discloses the use of phytic acid or derivatives thereof to reduce background interference in this sort of assay. While this assay is very good at detecting low levels of protein in a fluid test sample such as urine, its resolution drops off dramatically at higher protein concentrations, particularly at protein concentrations greater than about 150 mg/dL. This method is a total protein assay since the response is not dependent on the type of protein present in the test sample. Thus, human serum albumin (HSA) at 15 mg/dL provides the same response as IgG at 15 mg/dL. Since total protein assays are useful in the detection of certain disease states, and the higher the total protein spillover into urine the more serious the potential problem, a total protein assay that provides a detectable response at high protein concentrations is desirable. The molybdate/tungstate assay, however, is not effective for the detection of high levels of protein, i.e. above about 150 mg/dL, because of the strong affinity of the dye for protein.

Other Possible Components

The assay device or component may contain any number of surfactants, detergents, background dyes, enhancer polymers or chelating agents that are known in the art for use with protein detection methods based on dye binding. These assay devices or components typically include a protic solvent such as a water/methanol mixture in the concentrations set out in Table 1. Typically, the solution will contain a chelating agent such a phytic acid and/or oxalic acid to inhibit or prevent interference from other components in the urine test sample. The acids in the paper dip process may be adjusted to a preferred pH of from about 2.4 to about 3 by adding sodium hydroxide or the like.

TABLE 1

Optional Components

| Ingredient | Function | Conc. Used | General Range |
|---|---|---|---|
| Water | Solvent | 95 mL | — |
| Methanol | Solvent | 5 mL | 0–40 mL |
| Phytic Acid | Chelator | 1 g (15 mM) | 0–500 mM |
| Oxalic Acid | Chelator | 0.11 g (12 mM) | 0–40 mM |

EXAMPLES

One example of forming a dry device, such as a diagnostic strip, includes dipping a material such as paper into an aqueous solution. The diagnostic strip may be made from various materials, but is typically made from paper attached to a plastic carrier. One example of a suitable paper is Ahlstrom 204. It is contemplated that these strips may be made from other materials such as natural or synthetic woven, or nonwoven materials.

According to one embodiment, a first aqueous solution is formed by the addition of three submixes (Submixes 1–3). To form Submix 1, 10 ml of methanol, 1.76 ml of 125 mM TRIS ((tris(hydroxymethyl)aminomethane)/methanol) and 44.0 mg of pyrogallol red were added together. These components were mixed from about 20 to about 30 minutes to form Submix 1. To form Submix 2, 4.10 g (3.20 mL) of 40% phytic acid, 8.00 mL of 5% aqueous PVA (polyvinyl alcohol) of 31–50K, 11.2 ml of 1N NaOH and 0.654 mL of 100 mg/mL of sodium molybdate, and 45.6 mL of water were added together. The NaOH was added to adjust the pH to approximately 2.3. These components were mixed for about 60 minutes to form Submix 2. To form Submix 3, 217.5 mg of disodium oxalate, 120.0 mL of 500 mM L-citrulline with a pH of 2.5, and 100.0 mg of Cibacron Brilliant Yellow were added together. The components were mixed for about 30 minutes to form Submix 3.

Submix 1 and Submix 2 were mixed together for about 10 minutes and then Submix 3 was added. The pH was 2.6 and the combined Submixes 1–3 was stabilized for 4 hours and adjusted to volume. Submixes 1–3 formed a First Dip solution of about 200 mL. The paper was dipped into the First Dip solution and dried in a three-stage oven at 50/50/70° C. with a 1 inch air flow. The paper being used was Ahlstrom 204 paper.

The paper was then dipped into a Second Dip solution of 160 mL. The Second Dip solution was made by mixing 144 mL of toluene, 16 mL of THF (stabilized), 0.48 g of KOK (a polypropyleneglycol carbonate) such as disclosed in U.S. Pat. No. 5,424,215 and 36.57 mg of DNHB (5,5" Dinitro-3',3",3,4,5,6-hexabromophenolsulfonephthalein). The paper was dried in a three-stage oven at 50°/50°/50° C. with a 1 inch air flow to form the active pad of the diagnostic strips. The diagnostic strips include the active pad that is adhered to a polymeric strip.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. In an assay for the determination of protein in an aqueous test fluid which comprises combining the test fluid with (a) a buffer selected from the group consisting of citrulline, cyanoacetic acid, methyl phosphonic acid, saccharin, or combinations thereof, the buffer is added in sufficient quantity to maintain the pH of the assay including the test fluid at a selected target pH range within a range of from about 2.0 to about 3.0 and (b) a dye having a pKa which enables it to operate as a protein indicator at the target pH range and whose affinity for protein is such that it will provide a detectable response in the presence of greater than about 15 mg/dL protein to thereby render the assay suitable for the detection of total protein in the test fluid.

2. The assay of claim 1, wherein the buffer is selected from the group consisting of cyanoacetic acid, methyl phosphonic acid, saccharin, or combinations thereof.

3. The assay of claim 1, wherein the buffer is added in a sufficient quantity to maintain the pH of the assay including the test fluid within a range of from about 2.4 to about 3.0.

4. The assay of claim 1, wherein the dye is a substituted phenolsulfonephthalein, pyrogallol red or combinations thereof.

5. The assay of claim 4, wherein the dye is a substituted phenolsulfonephthalein, the substituted phenolsufonephthalein is octasubstituted with amino, amido, aromatic, alkyl, hydroxyl, thio, carboxylic, alkoxy, ketoxy, acetyl, halogen, nitro, cyano, or combinations thereof.

6. The assay of claim 4, wherein the dye is a substituted phenolsulfonephthalein, the substituted phenolsulfonephthalein is substituted at the 5', 5" positions with nitro and at the 3', 3", 3, 4, 5 and 6 positions with chloride, bromide or iodide.

7. The assay of claim 4, wherein the dye is a substituted phenolsulfonephthalein, the substituted phenolsulfonephthalein is 5,5"-Dinitro-3',3",3,4,5,6-hexabromophenolsulfonephthalein or 5'-Nitro-5"-Iodo-3',3",3,4,5,6,-hexabromophenolsulfonephthalein.

8. The assay of claim 1, wherein the dye is pyrogallol red and further includes a molybdate or tungstate salt.

9. The assay of claim 1 wherein the buffer and dye are absorbed in a test strip of absorbent material.

10. The assay of claim 1, wherein the detectable response provides good resolution at protein concentrations of from about 15 to about 300 mg/dL.

11. The assay of claim 1, wherein the dye operates as a color indicator in the presence of protein at a pH within the range of from about 2.0 to about 3.0.

12. The assay of claim 11, wherein the dye operates as a color indicator in the presence of protein at a pH within the range of from about 2.4 to about 3.0.

13. The assay of claim 1, wherein the buffer maintains the pH of the assay including the test fluid at a target pH plus or minus about 0.2 pH units.

14. In an assay for the determination of protein in an aqueous test fluid which comprises combining the test fluid with (a) a buffer selected from the group consisting of citrulline, cyanoacetic acid, methyl phosphonic acid, saccharin, or combinations thereof, the buffer is added in sufficient quantity to maintain the pH of the assay including the test fluid within about +/−0.2 pH units of a target pH range within a range of from about 2.0 to about 3.0 and (b) a dye having a pKa which enables it to operate as a color indicator in the presence of protein at the target pH range and whose affinity for protein is such that it will provide a detectable response in the presence of greater than about 2 to about 500 mg/dL protein to thereby render the assay suitable for the detection of total protein in the test fluid.

15. A dry device for use in an assay for determining protein levels in a fluid test sample which comprises an absorbent material having absorbed therein (a) a buffer selected from the group consisting of citrulline, cyanoacetic acid, methyl phosphonic acid, saccharin, or combinations thereof, the buffer is added in sufficient quantity to maintain the pH of the assay including the test fluid at a selected target pH range within a range of from about 2.0 to about 3.0 and (b) a dye having a pKa which enables it to operate as a protein indicator at the target pH range and whose affinity for protein is such that it will provide a detectable response in the presence of greater than 15 mg/dL protein upon contact between the device and the fluid test sample to thereby render the device suitable for the detection of total protein in the fluid test sample.

16. The dry device of claim 15, wherein the buffer is selected from the group consisting of cyanoacetic acid, methyl phosphonic acid, saccharin, or combinations thereof.

17. The dry device of claim 15, wherein the buffer is added in a sufficient quantity to maintain the, pH of the assay including the test fluid within a range of from about 2.4 to about 3.0.

18. The dry device of claim 15, wherein the dye is a substituted phenolsulfonephthalein, pyrogallol red or combinations thereof.

19. The dry device of claim 18, wherein the dye is a substituted phenolsulfonephthalein, the substituted phenolsulfonephthalein is octasubstituted with amino, amido, aromatic, alkyl, hydroxyl, thio, carboxylic, alkoxy, ketoxy, acetyl, halogen, nitro, cyano, or combinations thereof.

20. The dry device of claim 18, wherein the dye is a substituted phenolsulfonephthalein, the substituted phenolsulfonephthalein is substituted at the 5', 5" positions with nitro and at the 3', 3", 3, 4, 5 and 6 positions with chloride, bromide or iodide.

21. The dry device of claim 18, wherein the dye is a substituted phenolsulfonephthalein, the substituted phenolsulfonephthalein is 5,5"- Dinitro-3',3",3,4,5, 6-hexabromophenolsulfonephthalein or 5'-Nitro-5"-Iodo-3', 3",3,4,5,6,-hexabromophenolsulfonephthalein.

22. The dry device of claim 15, wherein the dye is pyrogallol red and further includes a molybdate or tungstate salt.

23. The dry device of claim 15, wherein the detectable response provides good resolution at protein concentrations of from about 15 to about 300 mg/dL.

24. The dry device of claim 15, wherein the dye operates as a color indicator in the presence of protein at a pH within the range of from about 2.0 to about 3.0.

25. The dry device of claim 24, wherein the dye operates as a color indicator in the presence of protein at a pH within the range of from about 2.4 to about 3.0.

26. The dry device of claim 15, wherein the buffer maintains the pH of the assay including the test fluid at a target pH plus or minus about 0.2 pH units.

27. A dry device for use in an assay for determining protein levels in a fluid test sample which comprises an absorbent material having absorbed therein (a) a buffer selected from the group consisting of citrulline, cyanoacetic acid, methyl phosphonic acid, saccharin, or combinations thereof, the buffer is added in sufficient quantity to maintain the pH of the assay including the test fluid within about +/−0.2 pH units of a selected target pH range within a range of from about 2.0 to about 3.0 and (b) a dye having a pKa which enables it to operate as a color indicator in the presence of protein at the selected target pH range and whose affinity for protein is such that it will provide a detectable response in the presence of from about 2 to about 500 mg/dL protein upon contact between the device and the fluid test sample to thereby render the device suitable for the detection of total protein in the fluid test sample.

28. In an assay for the determination of protein in an aqueous test fluid which comprises combining the test fluid with (a) as a buffer citrulline, the buffer is added in sufficient quantity to maintain the pH of the assay including the test fluid at a selected pH range within a range of from about 2.0 to about 3.0 and (b) a dye having a pKa which enables it to operate as a protein indicator at the target pH range and whose affinity for protein is such that it will provide a detectable response in the presence of greater than about 15 mg/dL protein to thereby render the assay suitable for the detection of total protein in the test fluid.

29. The assay of claim 28, wherein the dye is a substituted phenolsulfonephthalein, pyrogallol red or combinations thereof.

30. The assay of claim 28, wherein the dye operates as a color indicator in the presence of protein at a pH within the range of from about 2.0 to about 3.0.

31. The assay of claim 30, wherein the dye operates as a color indicator in the presence of protein at a pH within the range of from about 2.4 to about 3.0.

32. A dry device for use in an assay determining protein levels in a fluid test sample which comprises an absorbent material having absorbed therein (a) as a buffer citrulline, the buffer is added in sufficient quantity to maintain the pH of the assay including the test fluid at a selected target pH range within a range of from about 2.0 to about 3.0 and (b) a dye having a pKa which enables it to operate as a protein indicator at the target pH range and whose affinity for protein is such that it will provide a detectable response in the presence of greater than 15 mg/dL protein upon contact between the device and the fluid test sample to thereby render the device suitable for the detection of total protein in the fluid test sample.

33. The dry device of claim 32, wherein the dye is a substituted phenolsulfonephthalein, pyrogallol red or combinations thereof.

34. The dry device of claim 32, wherein the dye operates as a color indicator at a pH within the range of from about 2.0 to about 3.0 in the presence of protein.

35. The dry device of claim 34, wherein the dye operates as a color indicator at a pH within the range of from about 2.4 to about 3.0 in the presence of protein.

* * * * *